(12) United States Patent
Bodily

(10) Patent No.: US 12,419,721 B2
(45) Date of Patent: Sep. 23, 2025

(54) DENTAL LOUPES WITH BLACK LIGHT LENS

(71) Applicant: Coryn Bodily, St. George, UT (US)

(72) Inventor: Coryn Bodily, St. George, UT (US)

( * ) Notice: Subject to any disclaimer, the term of this patent is extended or adjusted under 35 U.S.C. 154(b) by 342 days.

(21) Appl. No.: 18/307,555

(22) Filed: Apr. 26, 2023

(65) Prior Publication Data
US 2023/0346509 A1 Nov. 2, 2023

Related U.S. Application Data

(60) Provisional application No. 63/336,625, filed on Apr. 29, 2022.

(51) Int. Cl.
| | |
|---|---|
| *A61B 90/50* | (2016.01) |
| *A61B 90/00* | (2016.01) |
| *A61B 90/30* | (2016.01) |
| *A61C 3/00* | (2006.01) |
| *F21W 131/20* | (2006.01) |
| *F21W 131/202* | (2006.01) |

(52) U.S. Cl.
CPC ............ *A61B 90/50* (2016.02); *A61B 90/361* (2016.02); *A61B 2090/3616* (2016.02); *A61B 2090/502* (2016.02); *A61C 3/00* (2013.01); *F21W 2131/20* (2013.01); *F21W 2131/202* (2013.01)

(58) Field of Classification Search
CPC ....... A61B 90/50; A61B 90/361; A61B 90/30; A61B 2090/3616; A61B 2090/502; A61B 17/00; A61B 18/00; A61B 3/006; F21W 2131/202; F21W 2131/20; A61C 3/00; G02B 2027/0187; G02B 3/00; G02B 2027/0938; G02B 2027/0955
See application file for complete search history.

(56) References Cited

U.S. PATENT DOCUMENTS

| | | |
|---|---|---|
| D592,693 S | 5/2009 | Chang |
| D602,185 S | 10/2009 | Chang |

(Continued)

OTHER PUBLICATIONS

Autodesk, I. J. (2023). Easiest Diy Black Light Out of Any Flashlight! Retrieved from https://www.instructables.com/Easiest-Diy-Black-Light-For-Making-Things-Glow/.

(Continued)

*Primary Examiner* — Paula J Stice
(74) *Attorney, Agent, or Firm* — Gurr & Brande, PLLC; Robert A. Gurr

(57) ABSTRACT

Dental loupes feature a light source, a composite lens, and a blacklight lens. Each lens may be hingedly coupled to the light source to prevent composite from curing or cause composite to fluoresce. The dental loupes have magnets for securing the position of each lens and/or may have a formfactor configured to allow ease of rotation and positioning. In some examples, the dental loupes include a first bracket coupled to and rotatable about a second bracket via a pin. The first bracket has a first aperture configured to hold a light source. The second bracket has a second aperture configured to hold a composite lens and a third aperture configured to hold a blacklight lens. In a first configuration, the light source aligns with the composite lens, preventing curing of composite. In a second configuration, the light source aligns with the blacklight lens, causing composite to fluoresce.

16 Claims, 7 Drawing Sheets

(56) References Cited

U.S. PATENT DOCUMENTS

| | | | |
|---|---|---|---|
| 10,107,483 B2 | 10/2018 | Oren | |
| 2021/0338082 A1* | 11/2021 | Steier | G02B 25/02 |
| 2022/0104909 A1* | 4/2022 | Winslow | A61B 90/30 |
| 2023/0333412 A1* | 10/2023 | Ruiz | G02B 25/004 |

OTHER PUBLICATIONS

Lumadent, Inc. (2023). Retrieved from https://www.lumadent.com/.
Orascoptic. (Oct. 3, 2022). Orascoptic™ granted U.S. patent for optical design used in headlights. Retrieved from https://www.orascoptic.com/en-us/news/orascoptic-granted-us-patent-for-optical-design-used-in-headlights?utm_medium=cpc&utm_source=google&utm_term=&utm_campaign=Hygienists&hsa_acc-8101871646&hsa_cam=6451469648&hsa_grp=79671758844&hsa_ad=460851483981&hsa_s.

* cited by examiner

DENTAL LOUPES WITH BLACK LIGHT LENS

CROSS-REFERENCE TO RELATED APPLICATIONS

This application claims the benefit of U.S. Provisional Application Ser. No. 63/336,625, filed on Apr. 29, 2022, which is incorporated herein by reference.

TECHNICAL FIELD

The present disclosure relates to dental loupes. More particularly, the present disclosure relates to dental loupes with a black light lens.

BACKGROUND

Composite bonding is a dental procedure that uses a fine layer of putty-like resin placed on top of natural teeth that is then shaped and molded to improve the appearance of one's smile. When done properly, the composite is difficult to distinguish from natural teeth. While this is an optimal result for the client, it can make charting and performing future treatments problematic for dental professionals. For example, it can be difficult to chart which teeth have been worked on in relation to those that have not been worked on. The composite also makes it more difficult to determine the integrity of marginal ridges and identify the borders of the teeth. A lack of accurate classification by dental professionals can lead to improper treatment and patient care.

Currently in the art, a provider reviews the teeth directly, often with the assistance of dental loupes, in an attempt to identify 1) teeth that may be in need of repair, and 2) teeth that have been repaired previously. Dental loupes allow a provider to ensure proper inspection and repair of teeth by magnifying the teeth. Even with magnifying the user's teeth, however, it can be difficult to locate repaired teeth, particularly by new students or providers. To overcome this problem, some students and providers use a blacklight to highlight composite. Still, handling a blacklight without sterilization can lead to contamination. Moreover, providers or their assistants must use a hand to hold the flashlight while performing treatment, crowding the area and limiting work efficiency. As a result, blacklights are not commonly used in the dental industry.

X-ray imaging, on the other hand, will actually highlight the portions of teeth that have composite. While this process may work for some patients, x-rays can be prohibitively expensive and time consuming for others. Proper identification of previously repaired teeth is thus difficult—particularly by a provider that is new to the industry or that has not had extensive training in identifying composite materials.

Accordingly, there is a need for a device that aids a provider in identifying previously repaired teeth that is fast, inexpensive, and sterile to use, allowing a provider to locate composite fillings, assess the integrity of margins, and illuminate calculus and biofilm. The present disclosure seeks to solve these and other problems.

SUMMARY OF EXAMPLE EMBODIMENTS

In some embodiments, dental loupes comprise a light source, a composite lens, and a blacklight lens. Each lens may be hingedly coupled to the light source, allowing each lens to be interchangeably pivoted over the light source. In some embodiments, dental loupes comprise a light source, a composite lens, and a blacklight lens. Each lens may swivel, interchangeably, to cover the light source. In some embodiments, the dental loupes may comprise magnets for securing the position of each lens. One or more lenses may comprise a formfactor configured to allow ease of rotation and positioning.

In some embodiments, dental loupes comprise a first bracket coupled to a second bracket by a pin or rod. The first bracket comprises a first aperture configured to hold a light source. The second bracket comprises a second aperture configured to hold a composite lens and a third aperture configured to hold a blacklight lens. The dental loupes comprise a first configuration, in which the second bracket is rotated about the first bracket such that the second aperture aligns with the first aperture, enabling a light source to emit light through the composite lens to prevent curing of any composite within a patient's mouth. The dental loupes comprise a second configuration, in which the second bracket is rotated about the first bracket such that the third aperture aligns with the first aperture. In the second configuration, the blacklight lens filters out visible light and emits ultraviolet light that causes composite within a patient's mouth to fluoresce.

DETAILED DESCRIPTION OF EXAMPLE EMBODIMENTS

Figure 1:
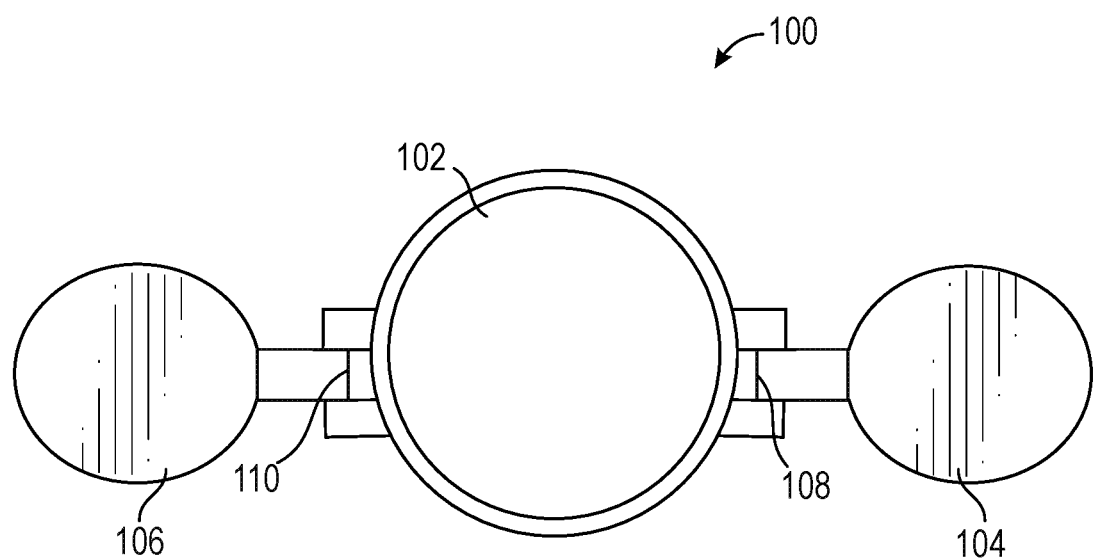
FIG. 1 illustrates a front elevation view of a light source and lenses of dental loupes.

The following descriptions depict only example embodiments and are not to be considered limiting in scope. Any reference herein to "the invention" is not intended to restrict or limit the invention to exact features or steps of any one or more of the exemplary embodiments disclosed in the present specification. References to "one embodiment," "an embodiment," "various embodiments," and the like, may indicate that the embodiment(s) so described may include a particular feature, structure, or characteristic, but not every embodiment necessarily includes the particular feature, structure, or characteristic. Further, repeated use of the phrase "in one embodiment," or "in an embodiment," do not necessarily refer to the same embodiment, although they may.

Reference to the drawings is done throughout the disclosure using various numbers. The numbers used are for the convenience of the drafter only and the absence of numbers in an apparent sequence should not be considered limiting and does not imply that additional parts of that particular embodiment exist. Numbering patterns from one embodiment to the other need not imply that each embodiment has similar parts, although it may.

Accordingly, the particular arrangements disclosed are meant to be illustrative only and not limiting as to the scope of the invention, which is to be given the full breadth of the appended claims and any and all equivalents thereof. Although specific terms are employed herein, they are used in a generic and descriptive sense only and not for purposes of limitation. Unless otherwise expressly defined herein, such terms are intended to be given their broad, ordinary, and customary meaning not inconsistent with that applicable in the relevant industry and without restriction to any specific embodiment hereinafter described. As used herein, the article "a" is intended to include one or more items. When used herein to join a list of items, the term "or" denotes at least one of the items, but does not exclude a plurality of items of the list. For exemplary methods or processes, the sequence and/or arrangement of steps described herein are illustrative and not restrictive.

It should be understood that the steps of any such processes or methods are not limited to being carried out in any particular sequence, arrangement, or with any particular graphics or interface. Indeed, the steps of the disclosed processes or methods generally may be carried out in various sequences and arrangements while still falling within the scope of the present invention.

The term "coupled" may mean that two or more elements are in direct physical contact. However, "coupled" may also mean that two or more elements are not in direct contact with each other, but yet still cooperate or interact with each other.

The terms "comprising," "including," "having," and the like, as used with respect to embodiments, are synonymous, and are generally intended as "open" terms (e.g., the term "including" should be interpreted as "including, but not limited to," the term "having" should be interpreted as "having at least," the term "includes" should be interpreted as "includes, but is not limited to," etc.).

As previously discussed, there is a need for a device that aids a provider in identifying previously repaired teeth that is fast, inexpensive, and sterile to use, allowing a provider to locate composite fillings, assess the integrity of margins, and illuminate calculus and biofilm. The dental loupes disclosed herein solve these and other problems.

Referring to FIG. 1, in some embodiments, dental loupes 100 comprise a light source 102, a composite lens 104, and a blacklight lens 106. The composite lens 104 may be hingedly coupled to a first side of the light source 102 via hinges 108. Likewise, the blacklight lens 106 may be hingedly coupled to a second side of the light source 102 via hinges 110. The hinges 108, 110 enable each lens 104, 106 respectively to be interchangeably pivoted over the light source 102. Both the composite lens 104 and the blacklight lens 106, without limitation, may be substantially round in shape, having a flat surface that corresponds to a surface of the light source 102.

The composite lens 104 is configured to isolate and filter out blue wavelength light having a wavelength between four hundred and five hundred nanometers to prevent curing and may be orange in color. The composite lens 104 enables a user to place and sculpt composite resin without it curing (i.e., hardening). When not required for curing, the composite lens 104 may be removed from the light source 102, allowing a user to use standard visible light without color distortions. The blacklight lens 106 is configured to filter out visible light from the light source 102 and emit ultraviolet light having a wavelength within a spectrum between two hundred and twenty-five and three hundred and ninety-five nanometers. In practice, the light emitted from the light source 102 passes through the blacklight lens 106 and then reflects off of fluorescent particles in the composites and resins creating an easily recognizable differentiation from natural enamel.

Most modern composite is a resin-modified glass ionomer cement having a powder containing a radiopaque fluoroaluminosilicate glass and a photoactive liquid. Other common composite compounds include bisphenol A-glycidyl methacrylate and related dimethacrylate monomers. Each of these composites comprise materials with high fluorescence that appear lighter (i.e., whiter) than natural enamel under blacklight radiation. Some restorative materials, such as temporary crowns and bridges made of acrylic or plastic, may appear less fluorescent because of a lack of fillers or density, but are still more fluorescent than enamel. In addition, temporary crowns and bridges have distinct outlines that differentiate them from caries and other dental health conditions that may be observed to fluoresce, which have a more diffuse outline. Thus, it will be appreciated that blacklight emitted from the dental loupes 100 permit a user to readily distinguish between many varieties of composite materials from natural enamel, without extensive experience in the dental industry.

In some methods of use, a user may emit visible light from a light source 102 when reviewing a patient's mouth, pivot a blacklight lens 106 on hinges 108 so as to filter out the visible light from the light source 102 and emit ultraviolet light, thereby highlighting composite from previous repairs in the mouth. Once located and charted, a user may return the blacklight lens 106 to its first position, unobstructing the light source 102. When placing composite, a user may pivot the composite lens 104 to ensure the composite does not cure until desired by the user. As a result, a user may readily use a blacklight without requiring the use of one's hands and without the same concerns of contamination that occur with holding a light.

Figure 2:
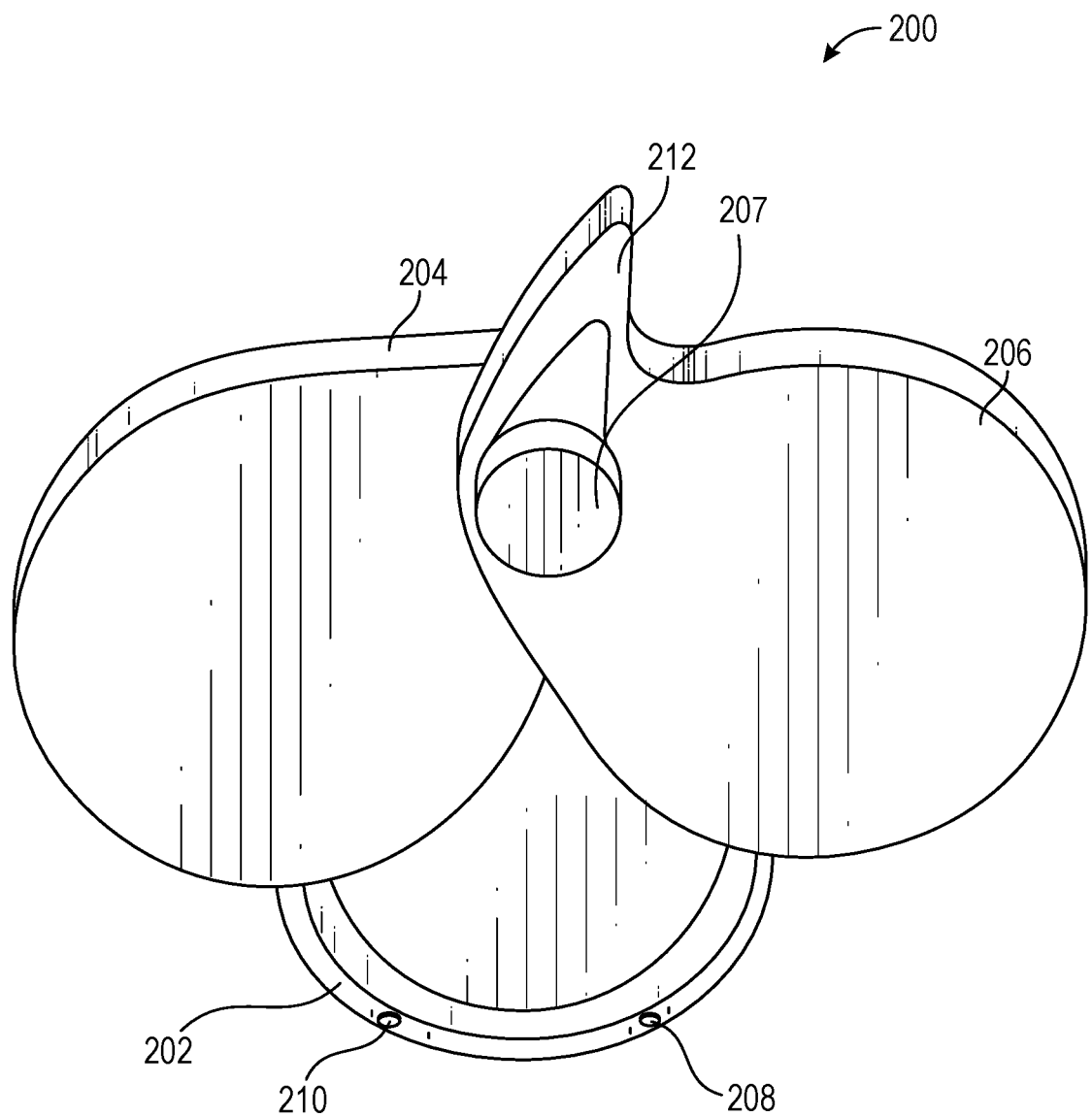
FIG. 2 illustrates a front perspective view of a light source and lenses of dental loupes.

Referring to FIG. 2, in some embodiments, dental loupes 200 comprise a light source 202, a composite lens 204, and a blacklight lens 206. Both the composite lens 204 and the blacklight lens 206 may swivel, interchangeably, to cover the light source 202. For example, the composite lens 204 and the blacklight lens 206 may each, respectively, rotate on a pin 207 or rod so as to either cover or uncover the light source 202. In some embodiments, the dental loupes 200 may comprise magnets 208, 210 for securing a position of each lens 204, 206. As appreciated, each lens 204, 206 may comprise a magnet or magnetic material for interacting with the magnetic force of magnets 208, 210 to thereby hold the position of each lens 208, 210 in the desired location. Additional magnets may be used to hold the lenses in an upward, unobstructing position as well.

In some embodiments, the lenses 204, 206 are stacked so that they may rotate on the pin 207. In this configuration, it is ideal for the composite lens 204 to be nearest to the light source 202 so as to ensure that the dental work is not adversely affected by the light (in other words, the composite lens 204 sufficiently blocks visible light from escaping unfiltered. However, even with the blacklight lens 206 separated from the light source 202 by a distance of the thickness of the composite lens 204, the blacklight effect still occurs, allowing a user to locate repaired teeth.

In some embodiments, one or more lenses may comprise a formfactor configured to allow ease of rotation. For example, the composite lens 204 and the blacklight lens 206 may each, respectively, comprise a protruding end, or hook 212, that allows for ease of rotation from one position to another by a user. It will be appreciated that either or both lenses 204, 206 may comprise a shape or formfactor for ease of rotation. In some embodiments, the lenses 204, 206 may be removably attachable to the dental loupes 200. While swiveling and pivoting has been discussed herein, it will be appreciated that the blacklight lens may couple to the dental loupes in a variety of manners and that such modifications are contemplated herein and within the scope of this disclosure.

Figure 3:
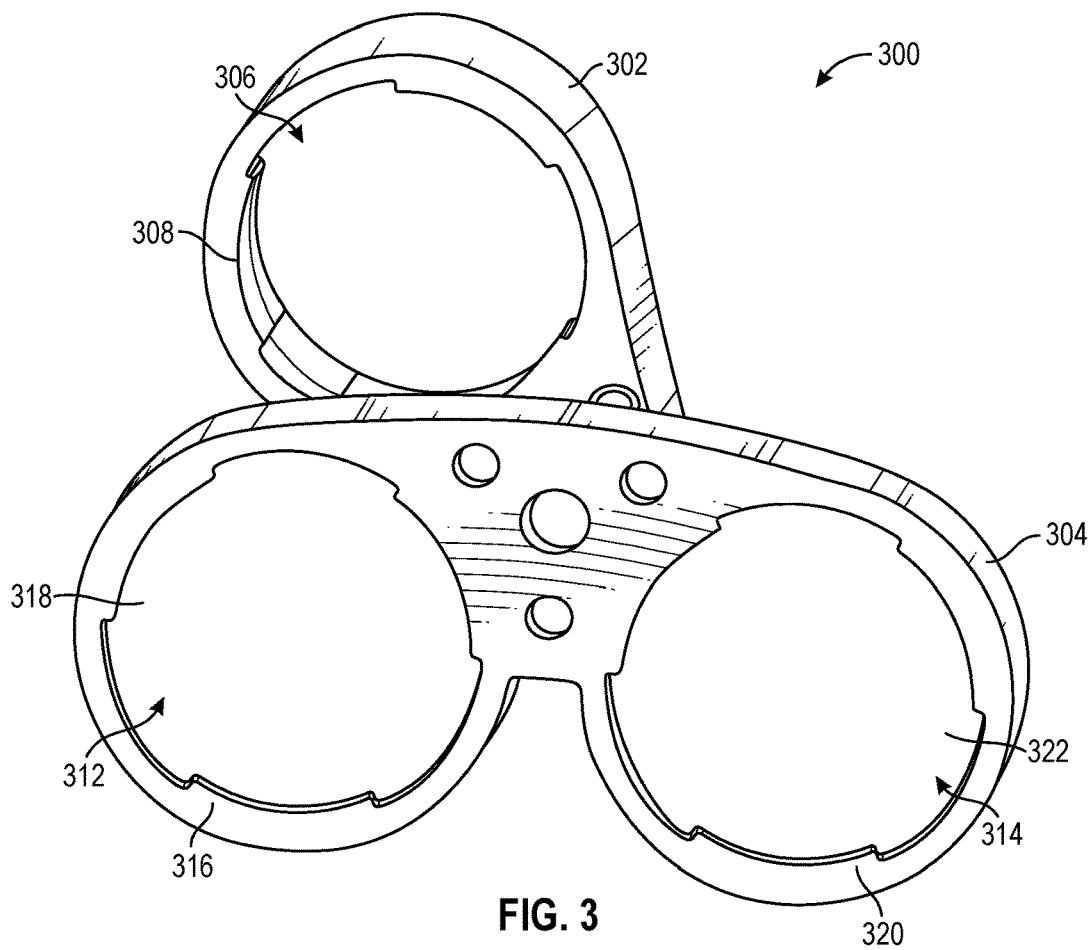
FIG. 3 illustrates a front perspective view of dental loupes.
Figure 4:
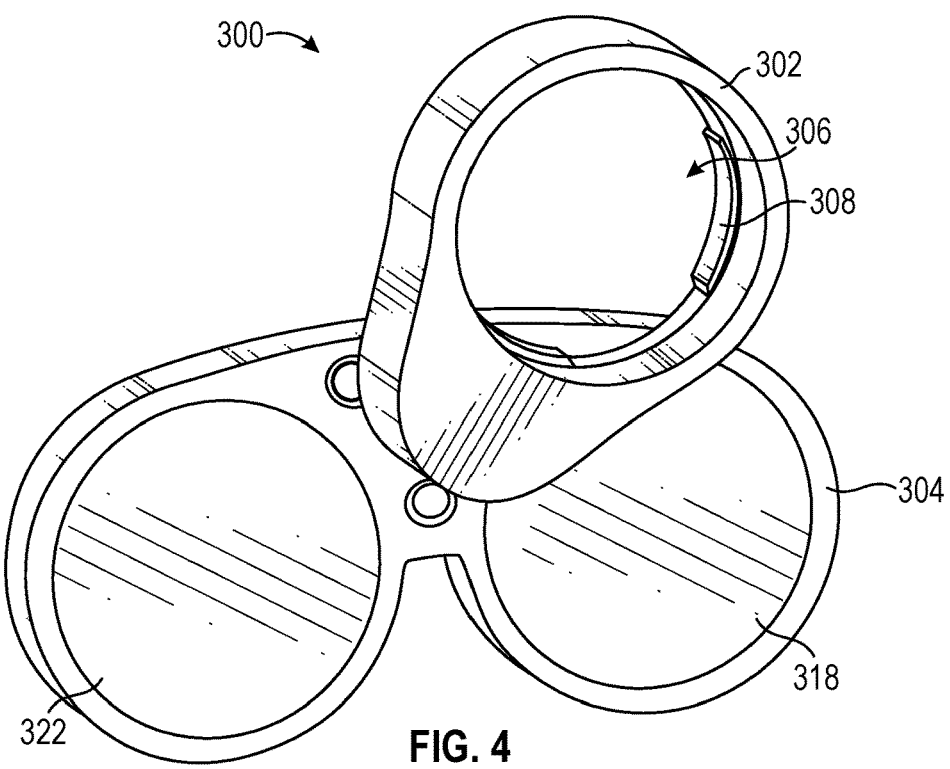
FIG. 4 illustrates a rear perspective view of dental loupes.
Figure 10:
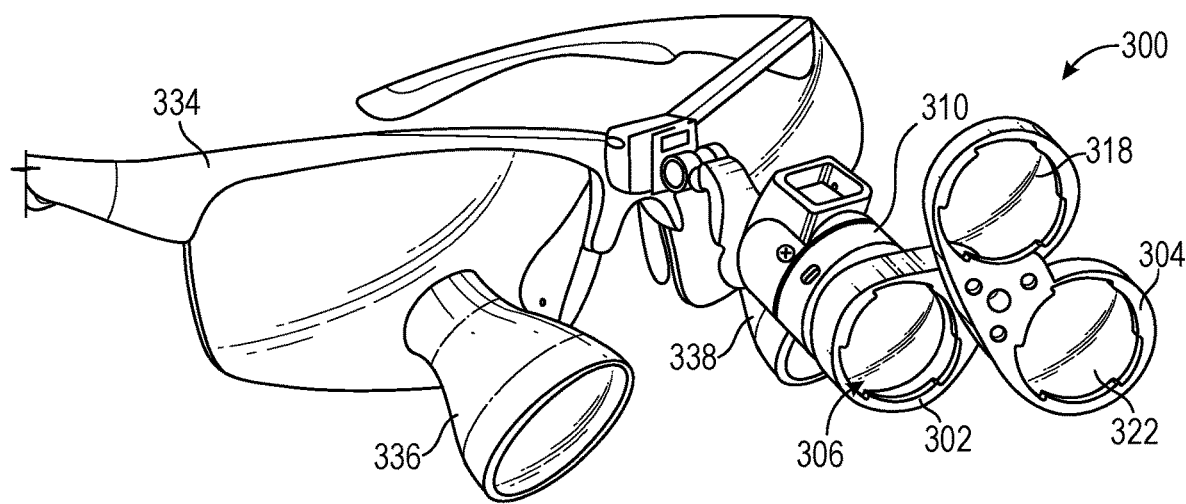
FIG. 10 illustrates a front perspective view of dental loupes mounted on eyewear.

Referring to FIGS. 3-4, in some embodiments, dental loupes 300 comprise a first bracket 302 and a second bracket 304 couplable to the first bracket 302. The first bracket 302 comprises a first aperture 306 having one or more protrusions 308 around a circumference of the first aperture 306, configured to hold a light source 310 (FIG. 10). The light source 310 may be snapped or screwed into the first aperture 306 such that a bulb of the light source 310 abuts the one or more protrusions 308 and emits light through the first aperture 306. The second bracket 304 comprises a second aperture 312 and a third aperture 314, opposite the second aperture 312. The second aperture 312 may comprise one or more protrusions 316 around a circumference of the first aperture 306, configured to hold a composite lens 318. The third aperture 314 may comprise one or more protrusions 320 around a circumference of the third aperture 314, configured to hold a blacklight lens 322. While one or more protrusions 308, 316, 320 are described in each of the apertures 306, 312, 314 respectively, it will be appreciated that other channels, slots, magnets, alternative fastening mechanisms (e.g., adhesive), or compression fit may be used to couple the light source 310, composite lens 318, and blacklight lens 322 therein, respectively.

Figure 5:
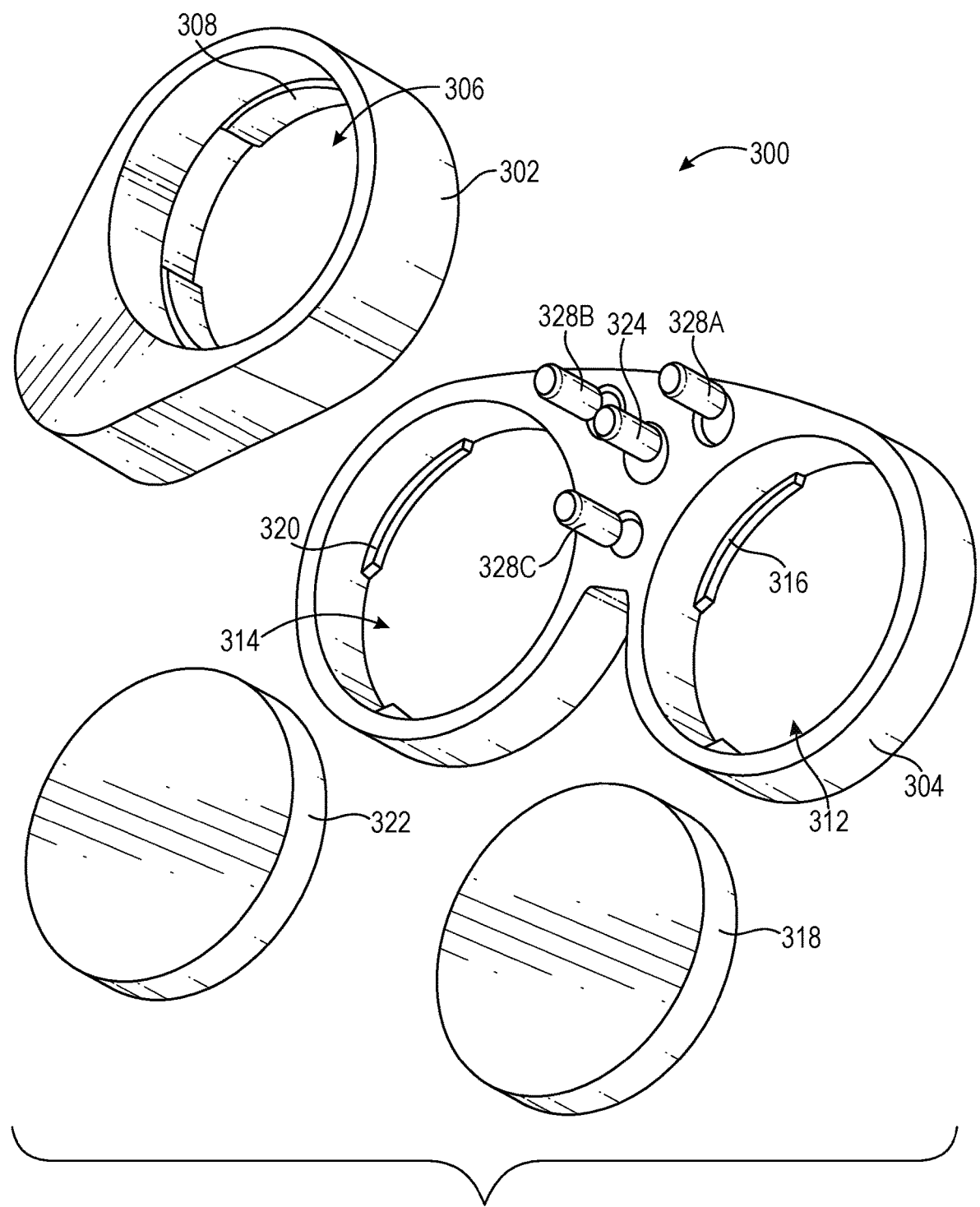
FIG. 5 illustrates an exploded view of dental loupes.
Figure 6:
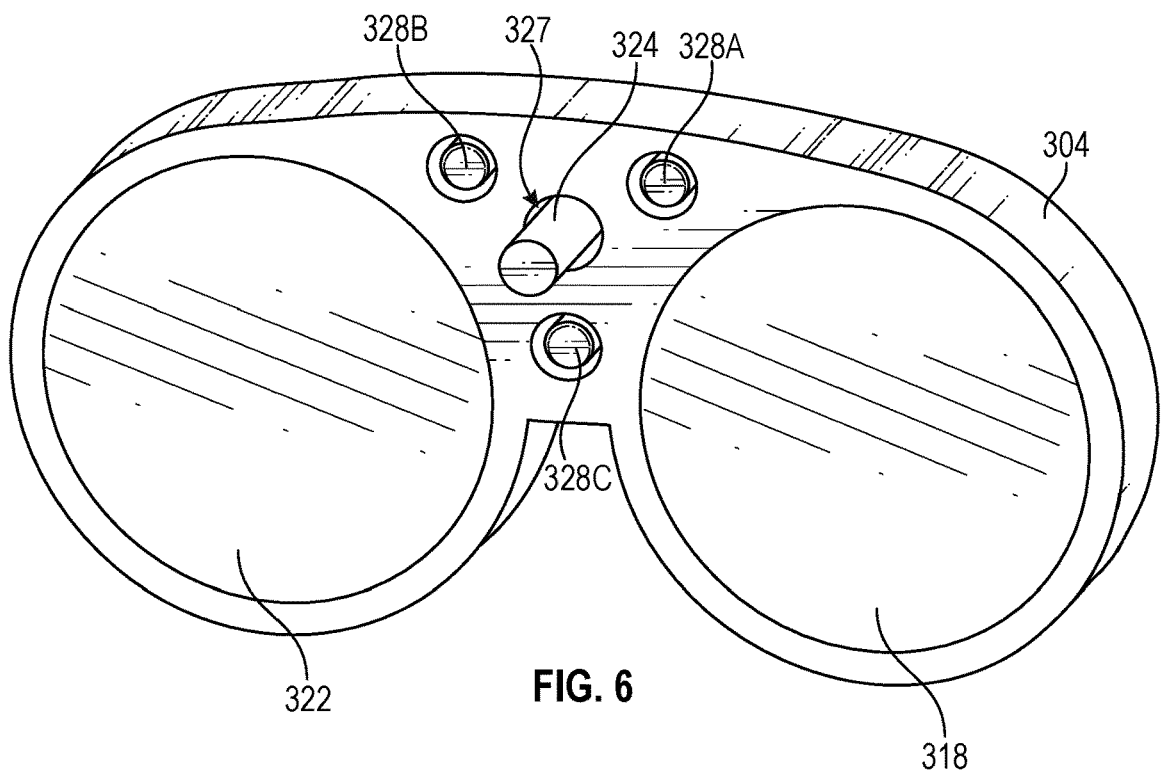
FIG. 6 illustrates a rear perspective view of a second bracket.
Figure 7:
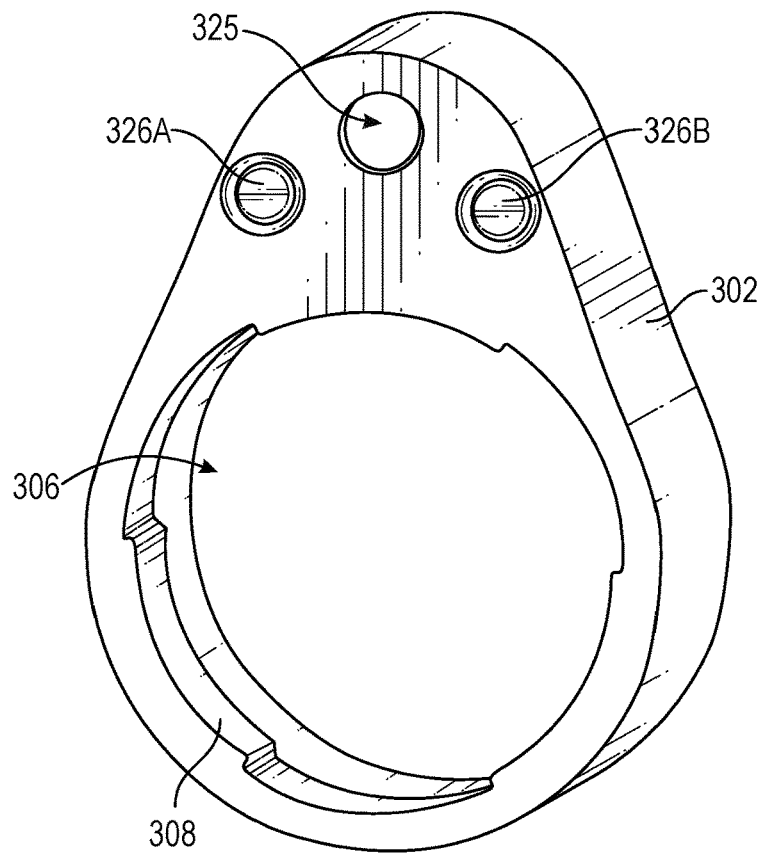
FIG. 7 illustrates a front perspective view of a first bracket.

As shown in FIGS. 5-7, a pin 324 or rod may be couplable between the first bracket 302 and the second bracket 304, extending therebetween, whereby the second bracket 304 is rotatable about a longitudinal axis of the pin 324. The pin 324 may extend between a first pin aperture 325 on the first bracket 302 and a second pin aperture 327 on the second bracket 304. In other words, a first portion of the pin 324 is received in the first pin aperture 325 and a second portion of the pin 324 is received in the second pin aperture 327, allowing the second bracket 304 to swivel thereon. While a pin 324 is shown and described, it will be appreciated that magnets may be used in place of the pin 324, allowing the entire second bracket 304 to be magnetically couplable to the first bracket 302. In this configuration, the magnets between the first bracket 302 and the second bracket 304 may be coupled in various configurations, allowing for differing alignments, as discussed later herein.

As best seen in FIGS. 6-7, one or more magnets 326A-B couplable to the first bracket 302 may be aligned in orientation and position with one or more magnets 328A-C on the second bracket 304. In some embodiments, the first bracket 302 may comprise two recesses or apertures, each fitted with one of the one or magnets 326A-B. The second bracket 304 correspondingly may comprise three recesses or apertures, each fitted with one of the one or more magnets 328A-C. The two recesses on the first bracket 302 are configured to align in orientation and position with the three recesses on the second bracket 304, enabling various configurations of the first bracket 302 relative to the second bracket 304, as discussed further below.

Figure 8:
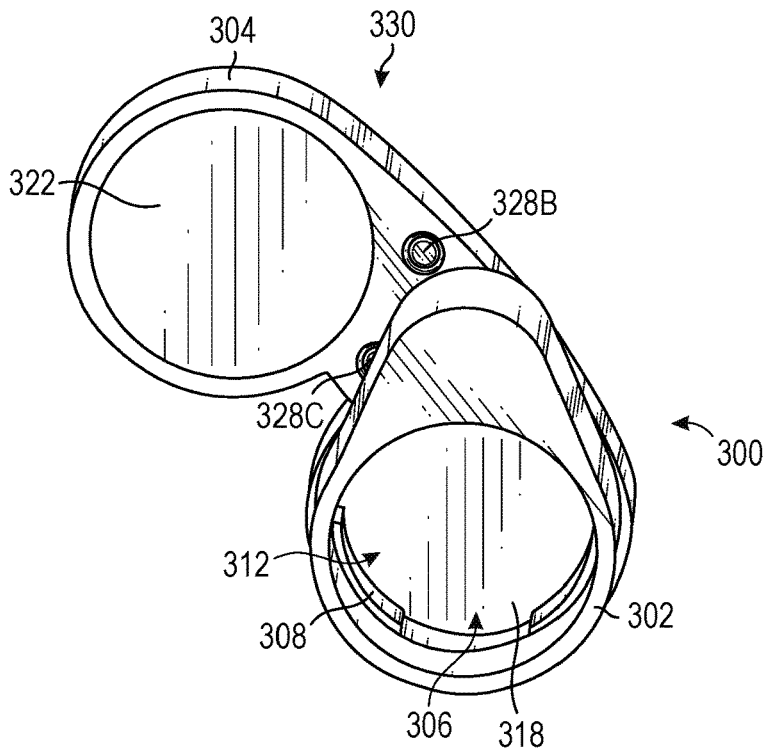
FIG. 8 illustrates a rear perspective view of dental loupes in a first configuration.

Referring to FIG. 8, in some embodiments, the dental loupes 300 may comprise a first configuration 330 in which the second bracket 304 is rotated about the first bracket 302 such that the second aperture 312 aligns with the first aperture 306. In said first configuration 330, the light source 310 (not shown in this Figure) emits light through the composite lens 318 to prevent curing of any composite within a patient's mouth. To maintain this configuration, a first magnet 326A couples to second magnet 328A and a third magnet 326B couples to fourth magnet 328C. They magnets hold this configuration until a user intervenes.

Figure 9:
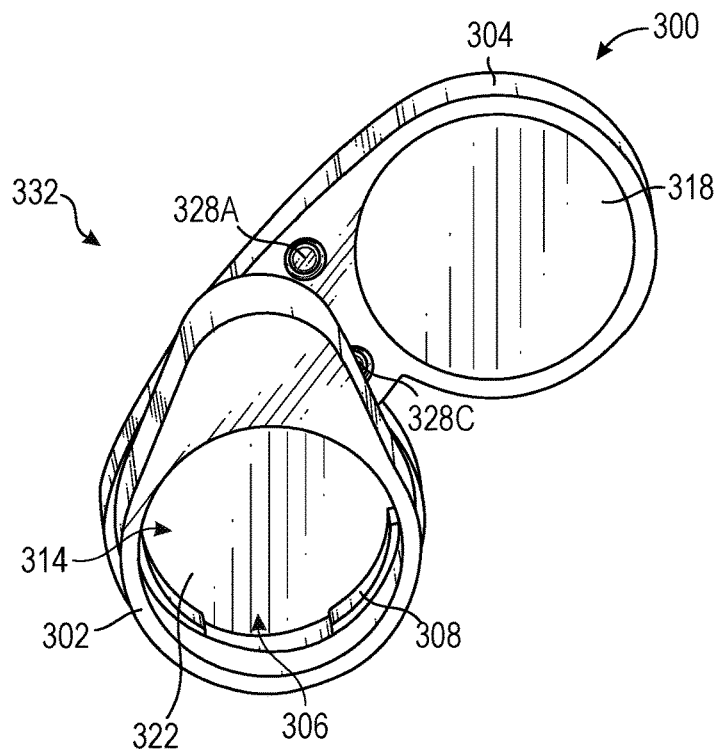
FIG. 9 illustrates a rear perspective view of dental loupes in a second configuration.

Similarly, as shown in FIG. 9, the dental loupes 300 may comprise a second configuration 332, in which the second bracket 304 is rotated about the first bracket 302 such that third aperture 314 aligns with the first aperture 306. In said second configuration 332, the light source 310 (not shown in this Figure) emits light through the blacklight lens 322 that is filtered into ultraviolet light, causing composite within a patient's mouth to fluoresce. The fluorescence then enables a user to clearly distinguish composite from enamel and identify marginal ridges. To maintain this configuration, the first magnet 326A couples to the fourth magnet 328C and the third magnet 326B couples to a fifth magnet 328B. Again, the magnets hold this configuration until a user intervenes.

As shown in FIG. 10, in some embodiments, the dental loupes 300 may comprise eyewear 334 and magnifying lenses 336, 338. The first aperture 306 of the first bracket 302 may be coupled to the light source 310. The light source 310 may be a head lamp or other light mounted to a frame of the eyewear 334 such as the bridge, whereby the user need not dedicate a hand to holding the dental loupes 300. Furthermore, it will be appreciated that a user need not touch the dental loupes 300 during dental examinations and procedures unless manipulating the dental loupes 300 between the first configuration 330 and the second configuration 332, or otherwise rotating the second bracket 304 from the first bracket 302 to produce natural light through aperture 306, as shown in FIG. 10. As needed, however, a user can remove the first and second brackets 302, 304 from the light source 310 to regularly clean and sterilize the dental loupes 300.

In some methods of use, a user may couple a first bracket 302 of dental loupes 300 to a light source 310, thereby emitting visible light while examining a patient's mouth. When placing composite, a user may rotate a second bracket 304 to a first configuration 330 whereby the light source 310 aligns with a composite lens 318. The composite lens 318 blocks light having a wavelength substantially between 400 and 500 nanometers to ensure the composite does not cure until desired by the user. The user may again rotate the second bracket 304 to a second configuration 332, whereby the light source 310 aligns with a blacklight lens 322. The blacklight lens 322 filters out visible light from the light source 310 and emits ultraviolet light therethrough, causing composite from previous repairs to fluoresce in the patient's mouth. The user may then distinguish the composite that brightly fluoresces from enamel that does not fluoresce to the same degree. As a result, a user may readily use a blacklight without requiring the use of one's hands and without the same limitations and concerns of contamination that occur with holding a flashlight.

It will be appreciated that by using the dental loupes 100, 200, 300 disclosed herein, a user may easily rotate between a standard light, a composite-compatible light that prevents composite from curing, and a blacklight that enables identification of composite from enamel, all while having both hands free to work. The dental loupes 100, 200, 300 further aid a user in identifying previously repaired teeth in a fast, inexpensive, and sterile manner, allowing a user to locate composite fillings, assess the integrity of margins, and illuminate calculus and biofilm. Therefore, the dental loupes 100, 200, 300 disclosed herein solve the problems in the prior art.

It will be appreciated that systems and methods according to certain embodiments of the present disclosure may include, incorporate, or otherwise comprise properties or features (e.g., components, members, elements, parts, and/or portions) described in other embodiments. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment unless so stated. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

Exemplary embodiments are described above. No element, act, or instruction used in this description should be construed as important, necessary, critical, or essential unless explicitly described as such. Although only a few of the exemplary embodiments have been described in detail herein, those skilled in the art will readily appreciate that many modifications are possible in these exemplary embodiments without materially departing from the novel teachings and advantages herein. Accordingly, all such modifications are intended to be included within the scope of this invention.

What is claimed is:

1. Dental loupes, comprising:
   a first bracket, comprising:
      a first aperture configured to couple to a light source, and
      a first pin aperture configured to receive a first portion of a pin;
   a second bracket, comprising:
      a second aperture comprising a composite lens,
      a third aperture comprising a blacklight lens, and
      and a second pin aperture configured to receive a second portion of the pin; and
   one or more magnets couplable between the first bracket and the second bracket,
   wherein the second bracket is configured to pivot in relation to the first bracket via the pin.

2. The dental loupes of claim 1, wherein in a first configuration the first aperture is aligned with the second aperture.

3. The dental loupes of claim 2, wherein the one or more magnets couplable between the first bracket and the second bracket are configured to engage each other, respectively, in the first configuration.

4. The dental loupes of claim 1, wherein in a second configuration the first aperture is aligned with the third aperture.

5. The dental loupes of claim 4, wherein the one or more magnets couplable between the first bracket and the second bracket are configured to engage each other, respectively, in the second configuration.

6. The dental loupes of claim 1, further comprising eyewear, wherein the light source is coupled to the eyewear and the first bracket is coupled to the light source.

7. Dental loupes, comprising:
   eyewear;
   a light source coupled to the eyewear;
   a composite lens coupled to the light source, the composite lens configured to rotate in and out of alignment with the light source; and
   a blacklight lens coupled to the light source, the blacklight lens configured to rotate in and out of alignment with the light source.

8. The dental loupes of claim 7, wherein the composite lens and the blacklight lens are each hingedly coupled to the light source.

9. The dental loupes of claim 7, wherein the composite lens and the blacklight lens are each coupled to the light source via a pin.

10. The dental loupes of claim 9, wherein the composite lens is closer to the light source than the blacklight lens.

11. The dental loupes of claim 10, wherein the composite lens and the blacklight lens each respectively comprise a protruding end.

12. The dental loupes of claim 7, wherein the composite lens and the blacklight lens are each coupled to the light source via magnets.

13. A method of using dental loupes, the method comprising:
    coupling a blacklight lens to a light source;
    filtering out visible light with the blacklight lens;
    emitting ultraviolet light through the blacklight lens;
    causing composite within a user's mouth to fluoresce; and
    identifying composite within a user's mouth by distinguishing composite that fluoresces.

14. The method of using dental loupes of claim 13, the method further comprising:
    coupling a composite lens to the light source; and
    filtering out light with the composite lens having a wavelength between 400 and 500 nanometers to prevent curing of the composite.

15. The method of using dental loupes of claim 13, the method further comprising:
    aligning a first aperture with a second aperture such that the light source is aligned with a composite lens.

16. The method of using dental loupes of claim 15, the method further comprising:
    aligning the first aperture with a third aperture such that the light source is aligned with the blacklight lens.

* * * * *